US006323173B1

(12) United States Patent
Winter et al.

(10) Patent No.: US 6,323,173 B1
(45) Date of Patent: Nov. 27, 2001

(54) 2-INDANMETHANOL DERIVATIVES AND THEIR USE IN PERFUMERY

(75) Inventors: Beat Winter, Bernex; Philippe Schneider, Geneva, both of (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/478,507

(22) Filed: Jan. 6, 2000

(30) Foreign Application Priority Data

Jan. 22, 1999 (CH) .................................................... 0123/99

(51) Int. Cl.[7] .................................................... A61K 7/46
(52) U.S. Cl. ................... 512/20; 512/17; 512/25; 512/26; 568/440; 568/592; 568/808; 510/101
(58) Field of Search .................. 512/17, 25, 26; 568/440, 592, 808; 510/101

(56) References Cited

U.S. PATENT DOCUMENTS 5,552,379    9/1996   Winter et al. ........................ 512/12

FOREIGN PATENT DOCUMENTS

| 0 365 015 A2 | 4/1990 | (EP) . |
| 0 685 444 | 12/1995 | (EP) . |
| 2 233 645 A | 1/1991 | (GB) . |
| WO 98/55439 | 12/1998 | (WO) . |

OTHER PUBLICATIONS

Liu et al., "α–Substitution of Ketones Via β–Keto Thiolesters", Tetrahedron Letters No. 43, pp. 4121–4124 (1979).
Shono et al., "New Synthesis of Cyclopropanes from 1,3–Dicarbonyl Compounds Utilizing Electroreduction of 1,3–Dimethanesulfonates", *J. Org. Chem.*, vol. 47, No. 16, pp. 3090–3094 (1982).

Sonnenbichler et al., "Synthesis of Compounds with Structural Similarities to the Toxic Metabolites of the Pathogenic Fungus *Heterobasidion annosum* and Investigation of Their Antibiotic Activities", *Biol. Chem. Hoppe–Seyler*, vol. 374, pp. 1047–1055 (1993).

Sonnenbichler J. et al. "Secondary fungal metabolites and their biological activities IV, Synthesis of compounds with structural similarities to the toxic metabolites of the pathogenic fungus *Heterobasidion annosum* and investigation of their antibiotic activities" Bio chem. Hoppe–Seyler XP–000874559, vol. 374 (11); pp. 1047–55 (1993).

*Primary Examiner*—Jill Warden
*Assistant Examiner*—Monique T. Cole
(74) *Attorney, Agent, or Firm*—Winston & Strawn

(57) ABSTRACT

The compounds of the formula (I)

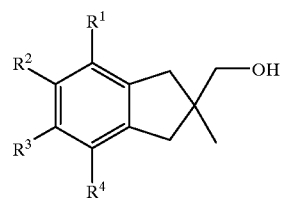

wherein the symbols $R^1$, $R^2$, $R^3$ and $R^4$ represent, independently of one another, a hydrogen atom or a linear or branched, saturated or unsaturated $C_1$ to $C_3$ lower alkyl radical, are advantageous as perfuming ingredients for the preparation of perfuming compositions and perfumed articles, to which they impart odoriferous notes of the lily of the valley type.

16 Claims, No Drawings

2-INDANMETHANOL DERIVATIVES AND THEIR USE IN PERFUMERY

The present invention relates to the field of perfumery. More particularly, it concerns the use of alcohols of the general formula

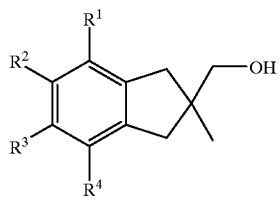

wherein the symbols $R^1$, $R^2$, $R^3$ and $R^4$ represent, independently of one another, a hydrogen atom or a linear or branched, saturated or unsaturated $C_1$ to $C_3$ lower alkyl radical as perfuming ingredients.

The compounds according to the invention have odoriferous characteristics of the lily of the valley type, which are very useful in perfumery. They also have numerous advantages, such as good stability in certain aggressive media for the perfume and excellent tenacity, which makes them particularly useful and advantageous for applications in the field of functional perfumery. For this reason, they can be used in the preparation of perfumes, perfuming compositions and perfumed articles.

The alcohols of the formula (I) develop a fresh, humic, very pleasant fragrance of the lily of the valley type. This fragrance is close to that of hydroxycitronellal (7-hydroxy-3,7-dimethyloctanal), although stronger than the latter. Its character can also be described as being between that of Lilial® [3-(4-tert-butylphenyl)-2-methylpropanal] and that of Lyral® [4-(4-hydroxy-4-methylpentyl)-3-cyclohexene-1-carbaldehyde].

The compound of the formula (I), wherein $R^1$, $R^2$, $R^3$ and $R^4$ each represent a hydrogen atom, i.e. 2-methyl-2-indanmethanol, has a structure known per se. Its synthesis has been described in literature by J. Sonnenbichler et al, Biol. Chem. Hoppe-Seyler (1993), 374(11), 1047–55, by Shono et al, Journal of Org. Chem. (1982), 47(16), 3090–4, and by Liu et al, Tetrahedron Lett. (1979), (43), 4121–4. However, in these references there is neither a description of the fragrance of 2-methyl-2-indanmethanol, nor a suggestion of its possible use in perfumery.

Furthermore, European patent application EP 685 444 describes aldehydes, some of which have a bicyclic structure similar to that of the compounds according to the invention. 5-tert-Butyl-2-indan-carbaldehyde and 6-tert-butyl-1-indanacetaldehyde are mentioned in particular. This application refers to the odoriferous properties of these compounds and their use in the field of perfumery. Although these known compounds are more stable than other, earlier aldehydes, the alcohols of the formula (I) according to the present invention have proved to be even more stable and advantageous, while having fragrances which are just as useful and also very long-lasting. Moreover, their odoriferous properties differ from those of these known aldehydes and bring new subtleties of fragrance to the perfumer's range.

Furthermore, the compounds of the formula (I), except for 2-methyl-2-indanmethanol, are new, and the invention also relates to these compounds.

Of the compounds according to the invention, the compounds of the formula (I) in which only two symbols selected from $R^1$, $R^2$, $R^3$ and $R^4$ represent a hydrogen atom, the two others being different, are more highly rated, in particular 2,5,6-trimethyl-2-indanmethanol or 2,4,6-trimethyl-2-indanmethanol, which both have a floral fragrance of the lily of the valley type, evoking hints of Lilial® and hydroxycitronellal.

The compounds (I) according to the invention are also highly rated, characterised in that only one of the symbols $R^1$ to $R^4$ is other than hydrogen. In the same way, 2,4-dimethyl-2-indanmethanol also has a floral fragrance of the lily of the valley type, like 2,5-dimethyl-2-indan-methanol, a preferred compound according to the invention.

The latter has a fresh fragrance of the lily of the valley type, close to the fragrance of hydroxycitronellal (7-hydroxy-3,7-dimethyloctanal), with a very highly rated, humic, lily of the valley background note, evoking the characteristic fragrance of Mayol® (cis-7-p-menthanol; origin: Firmenich SA, Geneva, Switzerland). This compound is distinguished from hydroxycitronellal in particular by its excellent tenacity, which makes it highly valued for its use in perfumery. Its long-lasting quality has proved to be superior to that of the aforementioned known aldehydes, but it is also distinctly superior to that of Mayol® (cis-7-p-menthanol). This characteristic has been confirmed in washing, on wet and dry laundry.

The aforementioned organoleptic properties are based on the compounds present in racemic form. Owing to their structure, the compounds (I) can also be present in an optically active form and have olfactory nuances distinct from the racemic compounds, enabling different fragrances to be obtained according to the isomer used. For example, while the fragrance of (+)-2,5-dimethyl-2-indanmethanol has a floral, lily of the valley note evoking the bottom note of Lilial®, (−)-2,5-dimethyl-2-indanmethanol is closer to hydroxycitronellal.

The compounds according to the invention lend themselves just as well to use in fine perfumery, in perfumes, eaux de toilette or after-shave lotions, as to other uses common in perfumery, such as the perfuming of soaps, shower gels or bath gels, hygiene or hair care products such as shampoos, and deodorants, air fresheners and cosmetic preparations.

The compounds (I) can also be used in liquid or solid detergents for the treatment of textiles, in fabric softeners and also in detergent compositions or cleaning products for washing up or for cleaning various domestic and industrial surfaces.

In these applications, the compounds according to the invention can be used alone or mixed with other perfuming ingredients, solvents or additives commonly used in perfumery. The nature and variety of these co-ingredients do not require further description here, which in any case could not be exhaustive, the skilled person being able to select them on the basis of his general knowledge and according to the nature of the product to be perfumed and the desired olfactory effect.

These perfuming ingredients belong to chemical classes as varied as alcohols, aldehydes, ketones, esters, ethers, acetates, nitrites, terpene hydrocarbons, nitrogenous or sulfurous heterocyclic compounds and essential oils of natural or synthetic origin. A lot of these ingredients are also listed in reference texts such as the book by S. Arctander, Perfume and Flavor Chemicals, 1969, Montclair, N.J., USA, or its more recent versions, and in other works of a similar nature.

The proportions in which the compounds according to the invention can be incorporated into the various aforementioned products vary within a wide range of values. These values depend on the nature of the article or product that one wishes to perfume and on the desired olfactory effect, as well as the nature of the co-ingredients in a given composition when the compounds according to the invention are mixed with perfuming co-ingredients, solvents or additives commonly used in the art.

As an example, typical concentrations are in the order of 5% to 10% by weight, even 20% or more by weight, of the compounds (I) according to the invention, based on the weight of perfuming composition into which they are incorporated. Lower concentrations can be used when the compounds are applied directly in the perfuming of the various consumables mentioned hereinabove.

The invention also relates to a general process for the preparation of the compounds according to the invention, characterised by hydrogenolysis of indanone of the formula

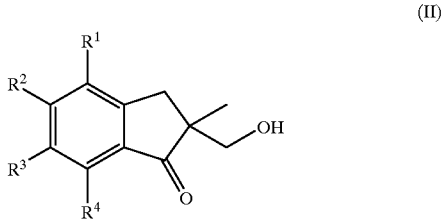

wherein the symbols $R^1$, $R^2$, $R^3$ and $R^4$ are as defined for the formula (I).

This step is carried out in conditions suitable for this type of reaction, which are known to the person skilled in the art. The starting material indanone is prepared from compounds which are known or which can be obtained in a conventional manner by reaction of aldol with formaldehyde (in any one of its forms), which can be represented by the following scheme:

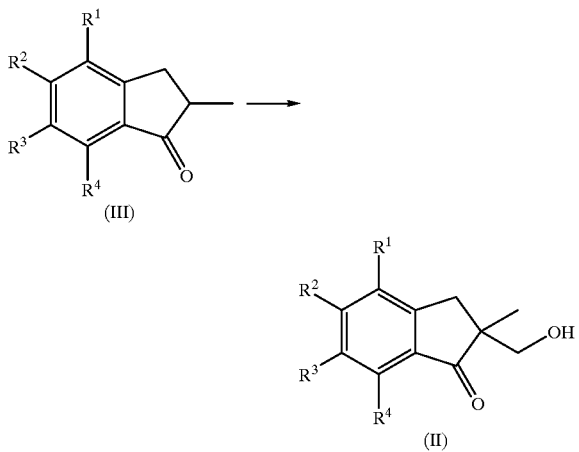

The compounds of the formula (II) are new compounds and form a subject of the invention.

The invention will now be described in further detail in the following examples, in which the temperatures are given in degrees Celsius and the abbreviations have the usual meaning in the art.

EXAMPLE 1

Preparation of 2,5-dimethyl-2-indanmethanol i) Preparation of the Racemic Mixture The synthesis of 2,5-dimethyl-2-indanmethanol was carried out in two stages starting from 2,6-dimethyl-1-indanone. The synthesis of the latter has been described in literature (see H. W. Pinnick, S. P. Brown, E. A. McLean, L. W. Zoller III in J. Org. Chem., 1981, 46, 3758).

a) Preparation of 2-hydroxymethyl-2,6-dimethyl-1-indanone from 2,6-dimethyl-1-indanone 147.53 g of $K_2CO_3$, 875 g of toluene and 350 g of 2,6-dimethyl indanone were introduced, under nitrogen, into a Schmizo-type 1.5 l vessel provided with a condenser and a mechanical stirrer. The mixture was heated to 51°. 122.45 g of Formcel® 55% (origin: Hoechst) were then added over a period of 1 h. The mixture was stirred continuously at 51° for 2 h. The reaction medium was then cooled to 24° and 350 g of water were added. After being stirred for 10 mins, the mixture was decanted, then washed 3 times with water. Concentration in vacuo produced 404.71 g of raw product pure to 97.6% (GC).

Analytical data:

IR ($CHCl_3$): 3430, 2910, 1685, 1600, 1485, 1380, 1035, 810 $cm^{-1}$

NMR($^1H$, 360 MHz, $CDCl_3$): 7.48(s, 1H); 7.40(d, J=8, 1H); 7.33(d, J=8, 1H); 3.82(d, J=11, 1H) 3.60(d, J=11, 1H); 3.22(d, J=16, 1H); 2.82(d, J=16, 1H); 2.78(broad, OH;)2.36 (s, 3H); 1.20(s, 3H)

NMR($^{13}C$, 90.5 MHz, $CDCl_3$): 211.4(s); 150.8(s); 137.4 (s); 136.5(d); 136.0(s); 126.3(d); 124.1(d); 67.6(t); 51.3(s); 37.6(t); 21.0(q); 20.7(q)

MS: 190($M^+$, 56), 175(65), 172(78), 159(100), 145(72), 129(73), 115(62), 104(27), 91(44), 77(33), 63(18), 51(20), 39(19), 31(21)

b) Preparation of 2,5-dimethyl-2-indanmethanol from 2-hydroxymethyl-2,6-dimethyl-1-indanone Pd—C at 5% (20 g) and methanesulfonic acid (2 g) were added t o a solution of product obtained under a) (200 g) in isopropanol (3000 g) and mixed under $H_2$ ($3 \times 10^3$ Pa) at 80° for 7½ hours. The mixture was absorbed in toluene (200 g) and washed successively with $H_2SO_4$ at 5%, $H_2O$, $NaHCO_3$ and $H_2O$, then concentrated in vacuo and finally distilled on residue ($0.08 \times 10^2$ Pa) to obtain 161.2 g of final product in the form of a colourless visco us liquid with a purity of 95.4% (GC).

Analytical data:

IR (pure): 3330(broad), 2910, 1485, 1035, 810$cm^{-1}$

NMR($^1H$, 360 MHz, $CDCl_3$): 7.04(d, J=8, 1H); 6.98(s, 1H); 6.93(d, J=8, 1H); 3.49(s, 2H); 2.87(d, J=16, 1H), 2.85(d, J=16, 1H); 2.60(d, J=16, 2H); 2.30(s, 3H); 1.80(s, OH); 1.16(s, 3H)

NMR($^{13}C$, 90.5 MHz, $CDCl_3$): 142.6(s); 139.4(s); 135.8 (s); 127.0(d); 125.5(d); 124.5(d); 70.5(t); 45.0(s); 42.7(t); 42.4(t); 24.0(q); 21.2(q)

MS: 176($M^+$, 33), 158(11), 143(100), 128(35), 115(21), 105(11), 91(11), 77(8), 51(6), 39(7), 31(15)

ii) Separation of the 2 optically active isomers

The two enantiomers of 2,5-dimethyl-2-indanmethanol were separated analytically by HPLC (high-pressure liquid chromatography) in a chiral column Chiralpack® AD (amylose-tris-3,5-dimethylphenyl carbamate, Daicel). Separation produced the enantiomers in pure form with an enantiomeric excess greater than 97%.

Analytical data:

(+)-2,5-dimethyl-2-indanmethanol $[\alpha]^D_{20}$=+3.2° (in $CHCl_3$ at 1.5%)

ee=99.4% (by HPLC)

Purity GC: >99.9%

(−)-2,5 -dimethyl-2-indanmethanol $[\alpha]^D_{20}$ =−3.2° (in $CHCl_3$ at 1.5%)

ee=97.3% (by HPLC)
Purity GC: >99.7%

EXAMPLE 2

Preparation of 2,4-dimethyl-2-indanmethanol

The synthesis of 2,4-dimethyl-2-indanmethanol was carried out in two stages starting from 2,7-dimethyl-1-indanone. The synthesis of the latter has been described by M. Fukuoka et al in Chem. Pharm. Bull., 1983, vol. 31, p. 3113.

a) Preparation of 2-hydroxymethyl-2,7-dimethyl-1-indanone from 2,7-dimethyl-1-indanone 0.51 g (3.7 mmol) of $K_2CO_3$ was added to a stirred solution of 1.17 g (7.3 mmol) of 2,7-dimethyl-1-indanone in 5 ml of toluene. The mixture thus obtained was heated to 50°. 0.42 ml (7.7 mmol) of Formcel® at 55% (origin: Hoechst) was added dropwise, causing slight exothermic reaction, and the mixture was stirred continuously at 50° for 4.5 h. The mixture was then poured into a bath of brine and ether; the organic phase was washed twice with brine, then dried offer $Na_2SO_4$ and concentrated to obtain 1.42 g of syrup. Crystallisation starting from a mixture of ether and pentane at −30° produced 0.77 g of colourless crystals (m.p. 93.5°–94°) and 0.51 g of solid mother liquor. Therefore, in total 1.29 g of product with a purity greater than 99% and a yield of 92% were obtained.

Analytical data:

IR($CHCl_3$): 3580, 3470, 2990, 2950, 2910, 2860, 1680, 1585, 1470, 1370, 1325, 1260, 1190, 1035, 980, 920 $cm^{-1}$

NMR($^1H$, 360 MHz, $CDCl_3$): 7.44(t, J=6, 1H); 7.27(d, J=6, 1H); 7.10(d, J=6, 1H); 3.79(dd, $J_1$=10, $J_2$=6, 1H); 3.60(dd, $J_1$=10, $J_2$=6, 1H); 3.18(d, J=16, 1H); 2.83 (d, J=16, 1H); 2.61(s, 3H); 2.57(m, OH); 1.22(s, 3H)

NMR($^{13}C$, 90.5 MHz, $CDCl_3$): 212.1(s); 153.9(s); 139.4(s); 134.4(d); 133.2(d); 129.3(d); 124.0(d); 67.9(t); 50.7(s); 37.5(t); 20.9(q); 18.3(q)

MS: 190($M^+$, 87), 175(33), 172(44), 159(100), 145(54), 129(41), 115(38), 103(11), 91(22), 77(13), 63(6), 51(5), 39(4)

b) Preparation of 2,4-dimethyl-2-indanmethanol from 2-hydroxymethyl-2,7-dimethyl-1-indanone 0.1 g of Pd—C at 10% was added to a solution of 0.67 g (3.5 mmol) of product obtained under a) in 10 ml of acetic acid and the mixture was stirred vigorously in an $H_2$ atmosphere ($10^5$ Pa) at ambient temperature for 6 days. The catalyst was filtered, and the filtrate concentrated in a rotary evaporator. The residue obtained was evaporated three times using toluene, finally producing 0.62 g of an opaque oil comprising 91% of the desired alcohol and 8% of the corresponding acetate. This raw product was absorbed in 1 ml of saponification mixture (2.5 N NaOH in EtOH—$H_2O$ 1:1), then heated to reflux (bath temperature 108°) over a period of 1 h. The cooled mixture was then poured into a mixture of brine and ether, the organic phase was washed with $NaHCO_3$ sat. aq. and brine, then dried over $Na_2SO_4$ and concentrated to obtain 0.60 g of a yellow oil. Bulb-to-bulb distillation (0.2×$10^2$ Pa, furnace temperature 75°–135°) produced 0.51 g of 2,4-dimethyl-2-indanmethanol with a purity greater than 99% and a yield of 83%.

Analytical data:

IR(pure): 3320(broad), 3020, 2900, 1585, 1455, 1370, 1030, 760 $cm^{-1}$

NMR($^1H$, 360 MHz, $CDCl_3$): 7.04(t, J=7, 1H); 6.99(d, J=7, 1H); 6.94(d, J=7, 1H) 3.50(s, 2H); 2.91(d, J=16,1H); 2.83(d, J=16,1H); 2.67(d, J=16, 1H); 2.58 (d, J=16, 1H); 2.21(s, 3H); 1.84(broad, OH); 1.18(s, 3H)

NMR($^{13}C$, 90.5 MHz, $CDCl_3$): 142.2(s); 141.3(s); 134.1(s); 127.0(d); 126.4(d); 122.1(d); 70.8(t); 44.2(s);43.0(t); 41.5(t); 24.3(q); 19.0(q)

MS: 176($M^+$, 32), 158(14), 143(100), 128(32), 115(18), 105(12), 91(10), 77(8), 51(6), 39(8), 31(7), 27(5)

EXAMPLE 3

Preparation of 2,5,6-trimethyl-2-indanmethanol

The synthesis of 2,5,6-trimethyl-2-indanmethanol was carried out in two stages starting from 2,5,6-trimethyl-1-indanone. The synthesis of the latter has been described by M. Fukuoka et al in Chem. Pharm. Bull., 1983, vol. 31, p. 3113.

a) Preparation of 2-hydroxymethyl-2,5,6-trimethyl-1-indanone from 2,5,6-trimethyl-1-indanone 0.97 g (10.7 mmol) of 1,3,5-trioxane (origin: Fluka) was added at ambient temperature to a stirred solution of 4.22 g (21.6 mmol) of 2,5,6-trimethyl-1-indanone in 20 ml of trifluoroacetic acid. The mixture thus obtained was heated to 50° over a period of 19 h. Once cooled, the mixture was diluted with ether, then washed with water and brine, the organic phase was dried over $Na_2SO_4$ and concentrated to obtain a brown liquid. Bulb-to-bulb distillation (0.35×$10^2$ Pa, furnace temperature 125°–145°) produced 5.4 g of corresponding trifluoroacetate. This product was dissolved in 12 ml of a 2.5 N solution of NaOH in EtOH—$H_2O$ 1:1, then heated to reflux over a period of 1h. Once cooled, the mixture was diluted with ether and water, the organic phase was washed with a saturated aqueous solution of $NaHCO_3$ and brine, then dried over $Na_2SO_4$ and concentrated to obtain 4.2 g of a yellow oil comprising 30% indanone and 59% keto-alcohol. Bulb-to-bulb distillation (0.3×10 Pa, furnace temperature 75°–145°) produced 1.95 g of a fraction enriched with 2-hydroxy-2,5,6-trimethyl-1-indanone with a yield of 32%.

Analytical data:

IR(pure): 3420, 2960, 2920, 2860, 1680, 1600, 1450, 1410, 1340, 1360, 1080, 950, 920, 890, 820 $cm^{-1}$ NMR($^1H$, 360 MHz, $CDCl_3$): 7.47(s, 1H); 7.22(s, 1H); 3.80(d, J=10, 1H); 3.59(d, J=10, 1H); 3.16(d, J=16, 1H); 2.80(d, J=16, 1H); 2.65(broad s, OH); 2.33(s, 3H); 2.27(s, 3H); 1.21(s, 3H)

NMR($^{13}C$, 90.5 MHz, $CDCl_3$): 211.1(s); 151.6(s); 145.6(s); 136.4(s); 133.9(s); 127.4(d); 124.5(d); 67.7(t); 51.0(s); 37.6(t); 20.8(q); 20.7(q); 19.7(q)

MS: 204($M^+$, 66), 189(74), 186(52), 173(100), 159(83), 143(42), 128(48), 115(50), 105(14), 91(31), 77(21), 63(11), 51(13), 39(14), 31(15)

b) Preparation of 2,5,6-trimethyl-2-indanmethanol from 2-hydroxymethyl-2,5,6-trimethyl-1-indanone 0.17 g of Pd—C at 10% was added to a solution of 1.79 g (6.8 mmol) of product obtained under a) in 35 ml of acetic acid and the mixture was stirred vigorously in an $H_2$ atmosphere ($10^5$ Pa) at ambient temperature for 12 days. The mixture was filtered over celite and concentrated in a rotary evaporator. The residue obtained was evaporated three times using toluene, finally giving 1.9 g of an oil comprising 60% of the desired alcohol, 11% of the corresponding acetate and 11% of intermediate diol. This raw product was diluted in 2 ml of a. 2.5 N solution of NaOH in EtOH—$H_2O$ 1:1, then heated to reflux over a period of 1 h. The mixture was then diluted with ether and water, the organic phase was washed with a saturated aqueous solution of NaHCO$_3$ and brine, then dried over Na$_2$SO$_4$ and concentrated to obtain 1.60 g of a yellow oil. Bulb-to-bulb distillation (0.4×10$^2$ Pa, furnace temperature 120°) produced 0.79 g of 2,5,6-trimethyl-2-indanmethanol with a purity of 91% and still containing 7% of intermediate diol. Flash chromatography over SiO$_2$ (79 g), using a mixture of toluene and ethyl acetate in a ratio of 4:1 as eluent, produced 0.69 g of purified product. Bulb-to-bulb distillation (0.7×10$^2$ Pa, furnace temperature 120 °) produced 0.69 g of desired product in the form of a colourless oil with a purity of 99% and a yield of 47%.

Analytical data:

IR(CHCl$_3$): 3590, 3440(broad), 2900, 1480, 1440, 1020 cm$^{-1}$

NMR($^1$H, 360 MHz, CDCl$_3$): 6.94(s, 2H); 3.50(s, 2H); 2.84(d, J=16, 2H); 2.58(d, J=16, 2H); 2.21(s, 6H); 1.67 (broad, OH); 1.16(s, 3H);

NMR($^{13}$C, 90.5 MHz, CDCl$_3$): 140.0(2s); 134.4(2s); 126.0(2d); 70.8(t); 45.0(s); 42.5(2t); 24.1(q); 19.7(2q);

MS: 190(M$^+$, 45), 172(16), 157(100), 142(17), 128(20), 115(11), 105(6), 91(7), 77(5), 51(3), 39(4), 31(4), 27(2)

EXAMPLE 4

Preparation of 2,4,6-trimethyl-2-indanmethanol

The synthesis of 2,4,6-trimethyl-2-indanmethanol was carried out in two stages starting from 2,4,6-trimethyl-1-indanone. The synthesis of the latter has been described by J. Colonge et al in Bull. Soc. Chim. Fr., 1951, p. 961.

a) Preparation of 2-hydroxymethyl-2,4,6-trimethyl-1-indanone from 2,4,6-trimethyl-1-indanone A stirred mixture of 0.53 g (3.04 mmol) of 2,4,6-trimethyl-1-indanone and 0.21 g (1.52 mmol) of K$_2$CO$_3$ in 5 ml of toluene was heated to 50°; 0.18 ml (3.34 mmol) of a solution at 55% of formaldehyde in methanol (Formcel® 55) was added dropwise thereto over a period of 1 min. The mixture thus obtained was stirred continuously at 50° for 2 h. Once cooled, the mixture was then diluted with ether and brine, the organic phase was washed twice with brine, then dried over Na$_2$SO$_4$ and concentrated to obtain 0.83 g of a yellowish oil. Crystallisation starting from ether at −30° produced 0.45 g of colourless cubic crystals (m.p. 110°) with a yield of 73%.

Analytical data:

IR(pure): 3396, 2914, 2869, 1674, 1615, 1482, 1380, 1309, 1250, 1047, 993, 871 cm$^{-1}$ NMR($^1$H, 360 MHz, CDCl$_3$): 7.35(s, 1H); 7.25(s, 1H); 3.82(dd, J$_1$=10, J$_2$=7, 1H); 3.62(dd, J$_1$=10, J$_2$=4, 1H); 3.08(d, J=17, 1H); 2.73(d, J=17, 1H); 2.56(m, OH); 2.35(s, 3H); 2.31(s, 3H); 1.23(s, 3H)

NMR($^{13}$C, 90.5 MHz, CDCl$_3$): 211.6(s); 149.8(s); 137.6 (s); 137.0(d); 135.7(s); 135.5(s); 68.0(t); 51.1(s); 36.6(t); 21.0(q); 20.8(q); 17.7(q)

MS: 204(M$^+$, 55), 189(18), 186(58), 173(100), 159(54), 143(28), 128(28), 115(24) 105(8), 91(13), 77(8), 63(4), 51(4), 39(4)

b) Preparation of 2,4,6-trimethyl-2-indanmethanol from 2-hydroxymethyl-2,4,6-trimethyl-1-indanone 0.1 g of Pd—C at 10% was added to a solution of 0.40 g (1.96 mmol) of product obtained under a) in 10 ml of acetic acid and the mixture was stirred vigorously in an H$_2$ atmosphere (1 Pa) at ambient temperature for 36 h. The catalyst was filtered and the filtrate concentrated to a colourless oil. This oil was absorbed in 2 ml of saponification mixture (2.5 N NaOH in EtOH—H$_2$O 1:1), then heated to reflux over a period of 0.5 h. The cooled mixture was then diluted with ether and NaHCO$_3$ sat. aq., the organic phase was washed twice with brine, then dried over Na$_2$SO$_4$ and concentrated to obtain 0.44 g of a yellowish oil. Bulb-to-bulb distillation (0.2×10$^2$ Pa, furnace temperature 100°–155°) produced 0.30 g of 2,4,6-1-trimethyl-2-indanmethanol in the form of a colourless oil with a purity of 98% and a yield of 78%.

Analytical data:

IR(pure): 3330(broad), 2900, 1470, 1370, 1030, 840cm$^{-1}$

NMR($^1$H, 360 MHz, CDCl$_3$): 6.82(s, 1H); 6.78(s, 1H); 3.50(s, 2H); 2.87(d, J=16, 1H); 2.78(d, J=16, 1H); 2.26(d, J=16, 1H); 2.53(d, J=16, 1H); 2.28(s, 3H); 2.18(s, 3H); 1.80(s, OH); 1.18(s, 3H)

NMR($^3$C, 90.5 MHz, CDCl$_3$): 142.4(s); 138.2(s); 136.1 (s); 133.8(s); 128.0(d); 122.8(d); 70.9(t); 44.4(s); 42.9(t); 41.1(t); 24.4(q); 21.1(q); 19.0(q)

MS: 190(M$^+$, 45), 172(14), 157(100), 142(18), 128(20), 115(12), 105(4), 91(5), 77(3), 51(2), 39(2), 31(2), 27(1)

EXAMPLE 5

Preparation of a Perfuming Composition for a Detergent

A base perfuming composition of the floral, lily of the valley type for a detergent was prepared by mixing the following ingredients:

| Ingredients | Parts by weight |
| --- | --- |
| Citronellyl acetate | 10 |
| cis-3-Hexenol acetate at 1%* | 20 |
| Hexyl cinnamic aldehyde | 200 |
| Benzyl acetone | 20 |
| cis-3-Hexenol at 1%* | 20 |
| Citronellol | 60 |
| Phenylethyl formate at 10%* | 20 |
| Geraniol | 80 |
| Synth. geranium | 5 |
| Geranyl nitrile[1] | 5 |
| Indole at 10%* | 10 |
| Linalool | 10 |
| 1-(5,5-Dimethyl-1-cyclohexen-1-yl)-4-penten-1-one[2] at 1%* | 20 |
| Methyl-2-nonynoate at 1%* | 10 |
| Rose oxide at 1%* | 20 |
| Ord. phenethylol | 70 |
| Synth. rose absolute at 10%* | 25 |
| Methyl N-(3-phenyl-1-butenyl)-anthranilate[3]* | 10 |
| Vert de Lilas[4] | 10 |
| Total | 625 |

*in dipropylene glycol
[1] 3,7-dimethyl-2,6-octadiene nitrile; origin: Firmenich SA, Geneva, Switzerland
[2] origin: Firmenich SA, Geneva, Switzerland
[3] origin: Firmenich SA, Geneva, Switzerland
[4] (2,2-dimethoxyethyl)benzene; origin: Firmenich SA, Geneva, Switzerland The addition of 375 parts by weight of 2,5-dimethyl-2-indanmethanol imparts to this base composition a superb, fresh, lily of the valley connotation, slightly green and powdered, and very diffusive. The odoriferous impact obtained with the compound according to the invention is comparable to that obtainable with Lilial® [3-(4-tert-butyl-1-phenyl)-2-methyl-propanal; origin: Givaudan-Roure SA], while remaining a lot more stable than that of the latter in detergents, in particular those containing TAED.

EXAMPLE 6

Preparation of a perfuming composition

A floral, lilac-type base composition was prepared from the following ingredients:

| Ingredients | Parts by weight |
|---|---|
| Anisic aldehyde | 30 |
| Ord. cinnamic alcohol at 50%* | 160 |
| Hedione ®[1] HC | 10 |
| Indole at 10%* | 20 |
| Linalool | 200 |
| Phenethylol | 100 |
| α-Terpineol | 350 |
| Vert de Lilas[2] | 30 |
| Total | 900 |

*in dipropylene glycol
[1] methyl dihydrojasmonate with a high cis-isomer content; origin: Firmenich SA, Geneva, Switzerland
[2] (2,2-dimethoxyethyl)benzene; origin: Firmenich SA, Geneva, Switzerland The addition of 100 parts by weight of 2,5-dimethyl-2-indanmethanol to this base composition produced a new composition, the fragrance of which had a pleasant floral/lilac connotation, far stronger, more natural and diffusive than that of the base composition.

EXAMPLE 7

Preparation of a Perfuming Composition for an eau de toilette for Women

A base composition for an eau de toilette for women was prepared from the following ingredients:

| Ingredients | Parts by weight |
|---|---|
| Benzyl acetate | 80 |
| Styralyl acetate | 5 |
| Ambrettolide | 30 |
| Astrotone[1] | 550 |
| Cassis base 345 B[2] | 35 |
| Cetalox ®[3] | 15 |
| cis-Jasmone | 15 |
| Allyl (cyclohexyloxy)acetate[4] at 10%* | 180 |
| Ethyl linalool | 250 |
| Violet leaves absolute at 10%* | 10 |
| 2-methyl-4-(2,2,3-trimethyl-3-cyclo-penten-l-yl)-4-penten-1-ol[5] at 10%* | 25 |
| Galaxolide ®50 MIP[6] | 1500 |
| Habanolide ®[7] | 210 |
| Hedione ®HC[8] | 2000 |
| Helional[9] | 200 |
| Indolene | 50 |
| Iralia[10] | 130 |
| Iso E Super[11] | 200 |
| Levocitrol | 24 |
| 3-Methyl-cyclopentadecenone[12] | 100 |
| Patchouli oil | 5 |
| Phenethylol | 190 |
| Pepper oil | 50 |
| Triplal ®[13] | 15 |
| Total | 6000 |

[1] 1,4-dioxa-5,17-cycloheptadecanedione; origin: Firmenich SA, Geneva, Switzerland
[2] origin: Firmenich SA, Geneva, Switzerland
[3] 8,12-epoxy-13,14,15,16-tetranorlabdanum; origin: Firmenich SA, Geneva, Switzerland
[4] origin: Firmenich SA, Geneva, Switzerland
[5] origin: Firmenich SA, Geneva, Switzerland
[6] 1,3,4,6,7,8-hexahydro-4,6,6,7,8,8-hexamethyl-cyclopenta-g-2-benzopyran; origin: International Flavors & Fragrances Inc., USA
[7] pentadecenolide: origin: Firmenich SA, Geneva, Switzerland
[8] methyl dihydrojasmonate with a high cis-isomer content; origin: Firmenich SA, Geneva, Switzerland
[9] 3-(1,3-benzodioxol-5-yl)-2-methylpropanal: origin: Firmenich SA, Geneva, Switzerland
[10] methylionone; origin: Firmenich SA, Geneva, Switzerland
[11] 1-(octahydro-2,3,8,8-tetramethyl-2-naphthalenyl)-1-ethanone; origin: International Flavors & Fragrances Inc., USA
[12] orgin: Firmenich SA, Geneva, Switzerland
[13] 2,4-dimethyl-3-cyclohex-1-ene-1-carboxyaldehyde; origin: International Flavors & Fragrances Inc., USA When 700 parts by weight of 2,5-dimethyl-2-indanmethanol were added to this modem eau de toilette, a new, transparent composition with a floral fragrance was obtained, the bottom note of which was even more radiant.

EXAMPLE 8

Preparation of a Perfuming Composition for an Eau de Toilette for Women

A base composition for an eau de toilette for women was prepared from the following ingredients:

| Ingredients: | Parts by weight |
|---|---|
| Vetiveryl acetate | 1000 |
| Hexyl cinammic aldehyde | 120 |
| Amione ®[1] | 5 |
| Benzophenone | 15 |
| Bergamot oil | 120 |
| Cedroxyde ®2) | 50 |
| Cetalox ®[3] at 10%* | 40 |
| California lemon oil | 20 |
| Citronellol | 110 |
| Coumarin | 20 |
| Galbanum oil at 10%* | 120 |
| Geraniol | 150 |
| Natural China geranium oil | 40 |
| English clove oil | 20 |
| Hedione ®[4]HC | 580 |
| Indole purified at 1%* | 40 |
| Iralia ®[5] | 460 |
| Synth. iris absolute | 20 |
| Isobutyl quinoline[6] at 10%* | 40 |
| Dalma oak moss absolute at 50%* | 20 |
| Oil of bitter-orange flowers, petals | 20 |
| Opopanax absolute | 20 |
| Ord. phenethylol | 580 |
| Rose absolute | 30 |
| Sandalwood oil | 100 |
| Undecalactone at 10%* | 20 |
| Vanillin at 10%* | 40 |
| Vertofix coeur[7] | 240 |
| Ylang | 160 |
| Total | 4300 | in dipropylene glycol
[1] allyl ionone; origin: Givaudan-Roure SA, Vernier, Switzerland
[2] trimethyl-13-oxabicyclo-[10.1.0]-trideca-4,8-diene; Firmenich SA, Geneva, Switzerland
[3] 8,12-epoxy-13,14,15,16-tetranorlabdanum; origin: Firmenich SA, Geneva, Switzerland
[4] methyl dihydrojasmonate; origin: Firmenich SA, Geneva, Switzerland
[5] mixture of iso-methyl iononones; origin: Firmenich SA, Geneva, Switzerland
[6] origin: International Flavors & Fragrances Inc., USA
[7] origin: International Flavors & Fragrances Inc., USA The addition of 400 parts by weight of 2,5-dimethyl-2-indanmethanol to this base composition imparts to it a fresh floral note and distinctly heightens the impact of the top note of the perfume, while increasing its diffusion during the course of evaporation.

What is claimed is:

1. A compound of the formula

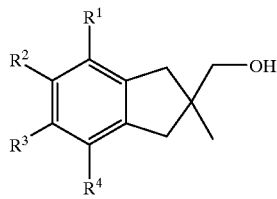

(I)

wherein the symbols $R^1$, $R^2$, $R^3$ and $R^4$ represent, independently of one another, a hydrogen atom or a linear or branched, saturated or unsaturated $C_1$ to $C_3$ lower alkyl radical, excluding the combination in which $R=R^2=R^3=R^4=H$.

2. A compound according to claim 1, wherein only two symbols selected from $R^1$, $R^2$, $R^3$ and $R^4$ represent a hydrogen atom.

3. A compound according to claim 1, wherein only one of the symbols selected from $R^1$, $R^2$, $R^3$ and $R^4$ represents a hydrogen atom.

4. A compound according to claim 2, wherein the symbols not representing a hydrogen atom represent a methyl radical.

5. A compound selected from 2,5-dimethyl-2-indanmethanol, 2,4-dimethyl-2-indanmethanol, 2,5,6-trimethyl-2-indanmethanol and 2,4,6-trimethyl-2-indanmethanol as a compound according to claim 4.

6. 2,5-Dimethyl-2-indanmethanol in racemic form or in the form of an optically active isomer as a compound according to claim 5.

7. A perfuming composition or perfumed article containing, together with perfuming ingredients, solvents, or adjuvants, a compound of formula.

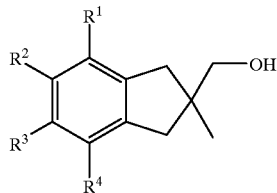

(I)

wherein the symbols $R^1$, $R^2$, $R^3$ and $R^4$ represent, independently of one another, a hydrogen atom or a linear or branched, saturated or unsaturated $C_1$ to $C_3$ lower alkyl radical, as an active perfuming ingredient.

8. A perfumed article according to claim 7 in the form of a perfume or eau de toilette, after-shave lotion, cosmetic preparation, soap, shampoo, conditioner or other hair care product, bath gel or shower gel, deodorant or air freshener, detergent or fabric softener or household product.

9. A process for the preparation of a compound according to claim 1, which comprises obtaining the compound hydrolysis of an indanone of the formula

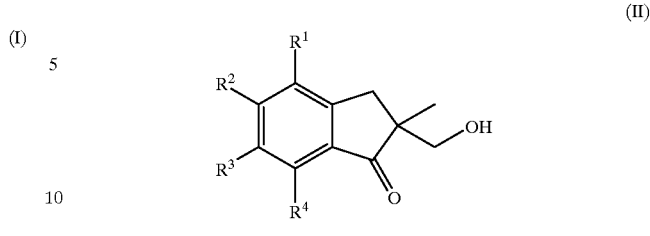

(II)

wherein the symbols $R^1$, $R^2$, $R^3$ and $R^4$ are as defined in claim 1.

10. A compound of the formula (II) as defined in claim 9.

11. A compound according to claim 10, wherein only two symbols selected from $R^1$, $R^2$, $R^3$ and $R^4$ in the formula (II) represent a hydrogen atom.

12. A compound according to claim 10, selected from the group comprising 2-hydroxymethyl-2,5-dimethyl-1-indanone, 2-hydroxymethyl-2,4-dimethyl-1-indanone, 2-hydroxymethyl-2,5,6-trimethyl-1-indanone and 2-hydroxymethyl-2,4,6-trimethyl-1-indanone.

13. A compound according to claim 10, wherein only one of the symbols selected from $R^1$, $R^2$, $R^3$ and $R^4$ in the formula (II) represent a hydrogen atom.

14. A compound according to claim 13, wherein the symbols not representing a hydrogen atom represent a methyl radical.

15. A compound according to claim 11, wherein the symbols not representing a hydrogen atom represent a methyl radical.

16. A method to confer, improve, enhance or modify the odor properties of a perfuming composition or a perfumed article, which method comprises adding as a perfuming ingredient to said composition or article a compound of formula:

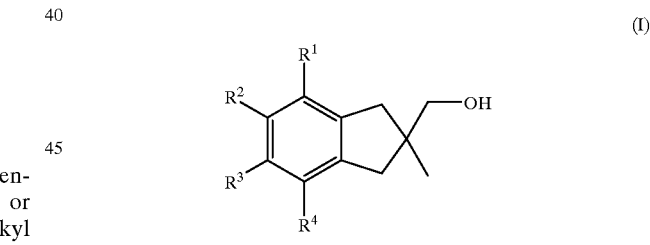

(I)

wherein the symbols $R^1$, $R^2$, $R^3$ and $R^4$ represent, independently of one another, a hydrogen atom or a linear or branched, saturated or unsaturated $C_1$ to $C_3$ lower alkyl radical, as an active perfuming ingredient.

* * * * *

UNITED STATES PATENT AND TRADEMARK OFFICE
CERTIFICATE OF CORRECTION

PATENT NO. : 6,323,173 B1
DATED : November 27, 2001
INVENTOR(S) : Winter et al.

It is certified that error appears in the above-identified patent and that said Letters Patent is hereby corrected as shown below:

Column 8,
Line 18, change "R=" to -- $R^1=$ --;
Line 34, after "formula", delete the period.

Column 9,
Line 1, before "hydrolysis", insert -- by --;
Line 50, delete ", as an active perfuming ingredient".

Signed and Sealed this

Twenty-fifth Day of June, 2002

Attest:

Attesting Officer

JAMES E. ROGAN
Director of the United States Patent and Trademark Office